United States Patent
Schmitt et al.

(10) Patent No.: US 8,666,020 B2
(45) Date of Patent: Mar. 4, 2014

(54) METHOD AND APPARATUS TO FILTER X-RAY BEAMS GENERATED USING A CT APPARATUS WITH DISPLACED GEOMETRY

(75) Inventors: Holger Schmitt, Hamburg (DE); Peter Forthmann, Sandesneben (DE); Udo Van Stevendaal, Ahrensburg (DE)

(73) Assignee: Koninklijke Philips N.V., Eindhoven (NL)

( * ) Notice: Subject to any disclaimer, the term of this patent is extended or adjusted under 35 U.S.C. 154(b) by 293 days.

(21) Appl. No.: 13/144,167

(22) PCT Filed: Dec. 9, 2009

(86) PCT No.: PCT/IB2009/055606
§ 371 (c)(1),
(2), (4) Date: Jul. 12, 2011

(87) PCT Pub. No.: WO2010/079393
PCT Pub. Date: Jul. 15, 2010

(65) Prior Publication Data
US 2011/0261923 A1    Oct. 27, 2011

Related U.S. Application Data

(60) Provisional application No. 61/143,856, filed on Jan. 12, 2009.

(51) Int. Cl.
*A61B 6/03*    (2006.01)
(52) U.S. Cl.
USPC .............................................. 378/8; 378/15

(58) Field of Classification Search
USPC ...................... 378/14–16, 156–158
See application file for complete search history.

(56) References Cited

U.S. PATENT DOCUMENTS

| | | | | |
|---|---|---|---|---|
| 5,677,943 A * | 10/1997 | Hoebel | | 378/156 |
| 2004/0258195 A1 * | 12/2004 | Hara | | 378/11 |
| 2006/0269044 A1 | 11/2006 | Fehre et al. | | |
| 2007/0217573 A1 | 9/2007 | Bernhardt | | |
| 2007/0238957 A1 * | 10/2007 | Yared | | 600/407 |
| 2008/0013689 A1 * | 1/2008 | Toth et al. | | 378/158 |

FOREIGN PATENT DOCUMENTS

WO    2008021671 A2    2/2008

* cited by examiner

*Primary Examiner* — Hoon Song
*Assistant Examiner* — Danielle Fox

(57) ABSTRACT

A method and apparatus are provided to filter x-ray beams generated using a CT apparatus or other x-ray based system with displaced acquisition geometry. A CT apparatus may be used having a source (102), a detector (104) transversely displaced from a center (114) of a field of view (118) during acquisition of the projection data, and a filter (146). The filter may absorb at least a portion of overlapping radiation emitted by the source at opposing angular positions. The amount of transverse displacement may be determined for a desired field of view configuration and amount of overlapping radiation. The detector may be adjusted to correspond to the amount of determined transverse displacement. The size and location of the filter may be determined based on the amount of overlapping radiation. The filter may be adjusted to correspond to the determined size and location of the filter.

25 Claims, 4 Drawing Sheets

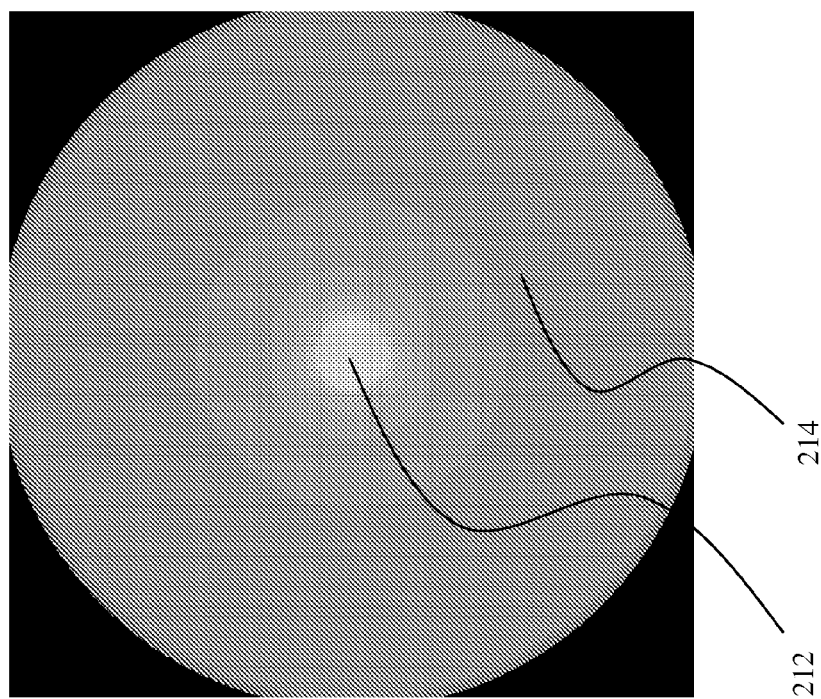
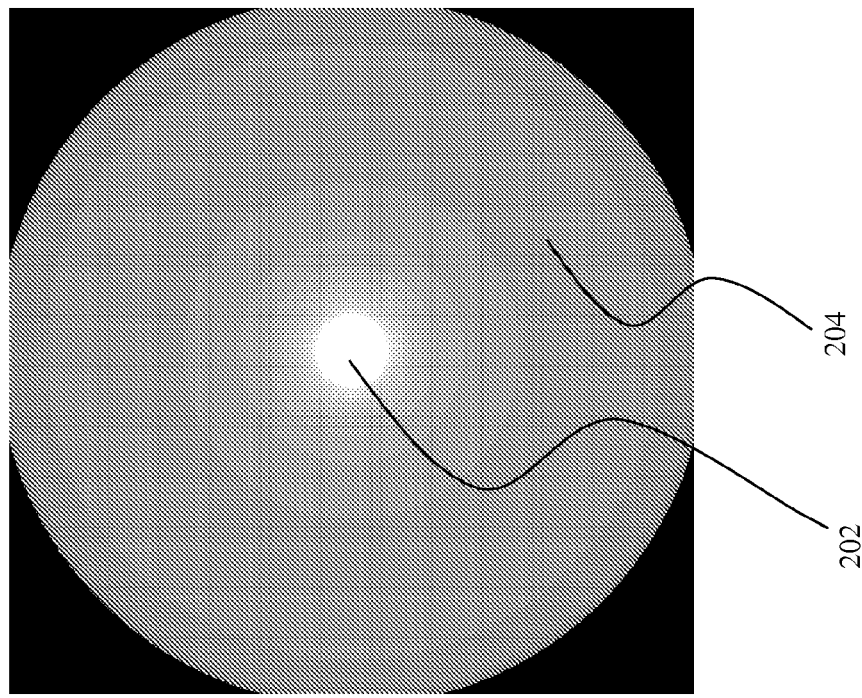

US 8,666,020 B2

METHOD AND APPARATUS TO FILTER X-RAY BEAMS GENERATED USING A CT APPARATUS WITH DISPLACED GEOMETRY

CROSS REFERENCE TO RELATED APPLICATIONS

This application claims the benefit of U.S. provisional application Ser. No. 61/143,856 filed Jan. 12, 2009, which is incorporated herein by reference.

The present application relates to computed tomography ("CT") systems and other x-ray based systems. In particular, it finds application in systems incorporating an offset x-ray source and detector.

Such systems find application in medical imaging, article and security inspection, non-destructive testing, pre-clinical imaging, and other situations in which x-ray data can provide useful information about the structure or function of an object. One area in which CT imaging systems have gained widespread acceptance is in medicine, where CT scanners are widely used by radiologists and other medical professionals in connection with the diagnosis and treatment of disease.

PCT International Application No. PCT/US2007/074201, filed on Jul. 24, 2007, which is incorporated herein by reference, describes a CT apparatus and method for acquiring projection data at a plurality of angular positions relative to an object disposed in an examination region. The CT apparatus includes an x-ray source and an x-ray detector transversely displaced from a transverse center of rotation in the transaxial plane (i.e., off-transverse center, offset, or off-focus). A CT apparatus having offset geometry is desirable because it allows for an increased field of view. The x-ray source and detector rotate about the transverse center of rotation and remain in a fixed mechanical relation to each other so as to acquire projection data at a plurality of projection angles. The CT apparatus reconstructs the projection data generated by the CT apparatus using reconstruction techniques, such as filtered backprojection, to generate volumetric data indicative of the object under examination.

The projections generated at opposing positions using a CT apparatus having an offset x-ray detector geometry will often overlap. The overlapping projection data is generally used by various reconstruction algorithms to generate volumetric data indicative of the object under examination. For each pair of opposing projections, some voxels in the image are reconstructed using the projection data from both projections while other voxels are reconstructed using data from one projection only. This difference in reconstruction results in an inhomogeneous signal to noise ratio ("SNR") distribution in the image. In other words, the overlapping projections increase the x-ray dose applied to the patient.

Aspects of the present invention address these matters, and others.

According to one aspect of the present invention, a method and apparatus are provided to filter x-ray beams generated in an x-ray based imaging system with displaced acquisition geometry.

Still further aspects of the present invention and related advantages will be appreciated to those of ordinary skill in the art upon reading the following detailed description. The invention may take form in various components and arrangements of components, and in various process operations and arrangements of process operations. The drawings are only for the purpose of illustrating preferred embodiments and are not to be construed as limiting the invention.

FIG. 2A is an exposure from a simulated CT scan with no x-ray dose reduction in the area of the detector receiving overlapping x-ray radiation;

FIG. 2B is an exposure from a simulated CT scan with a 50% x-ray dose reduction in the area of the detector receiving overlapping x-ray radiation;

Figure 3:
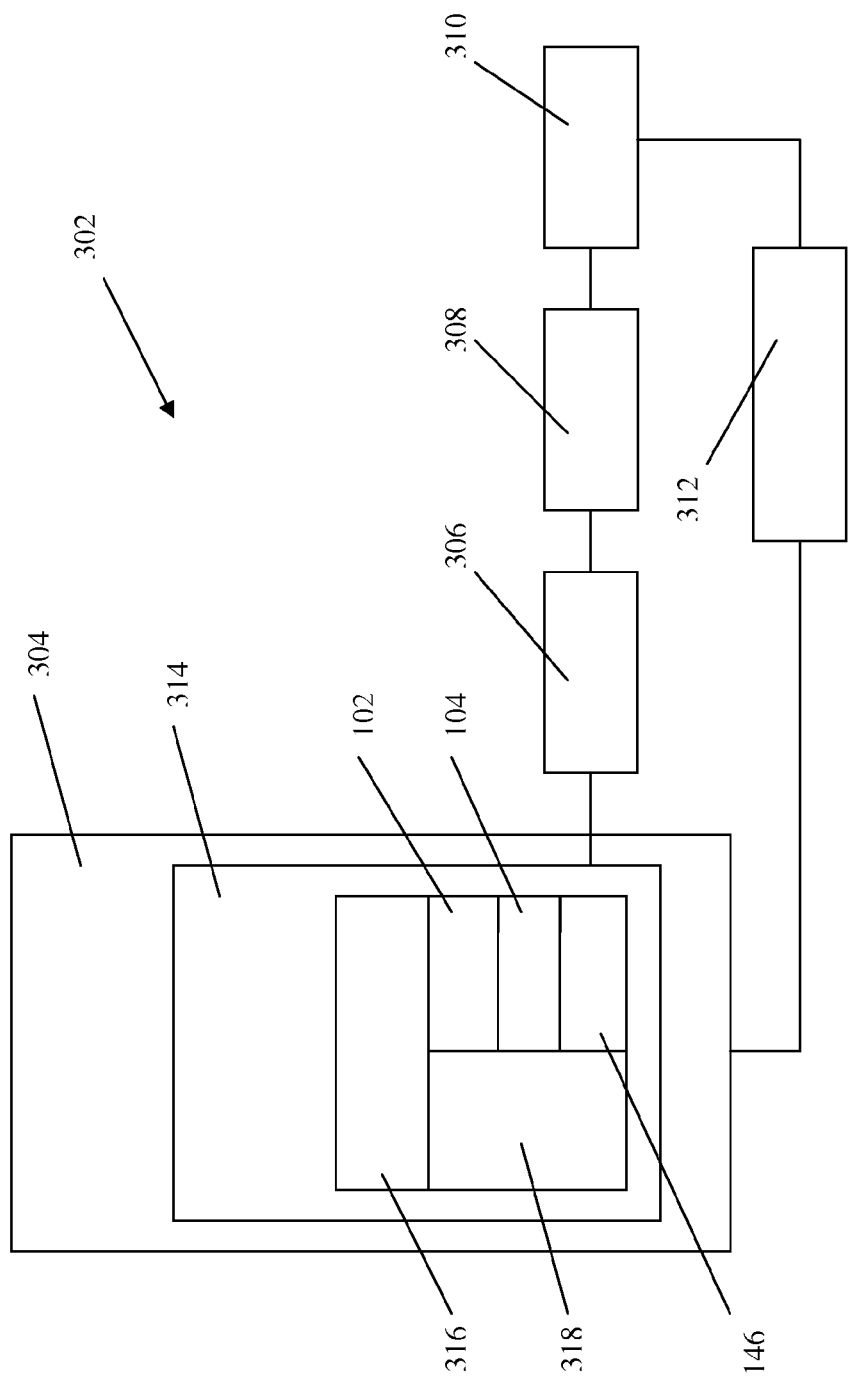
Figure 4:
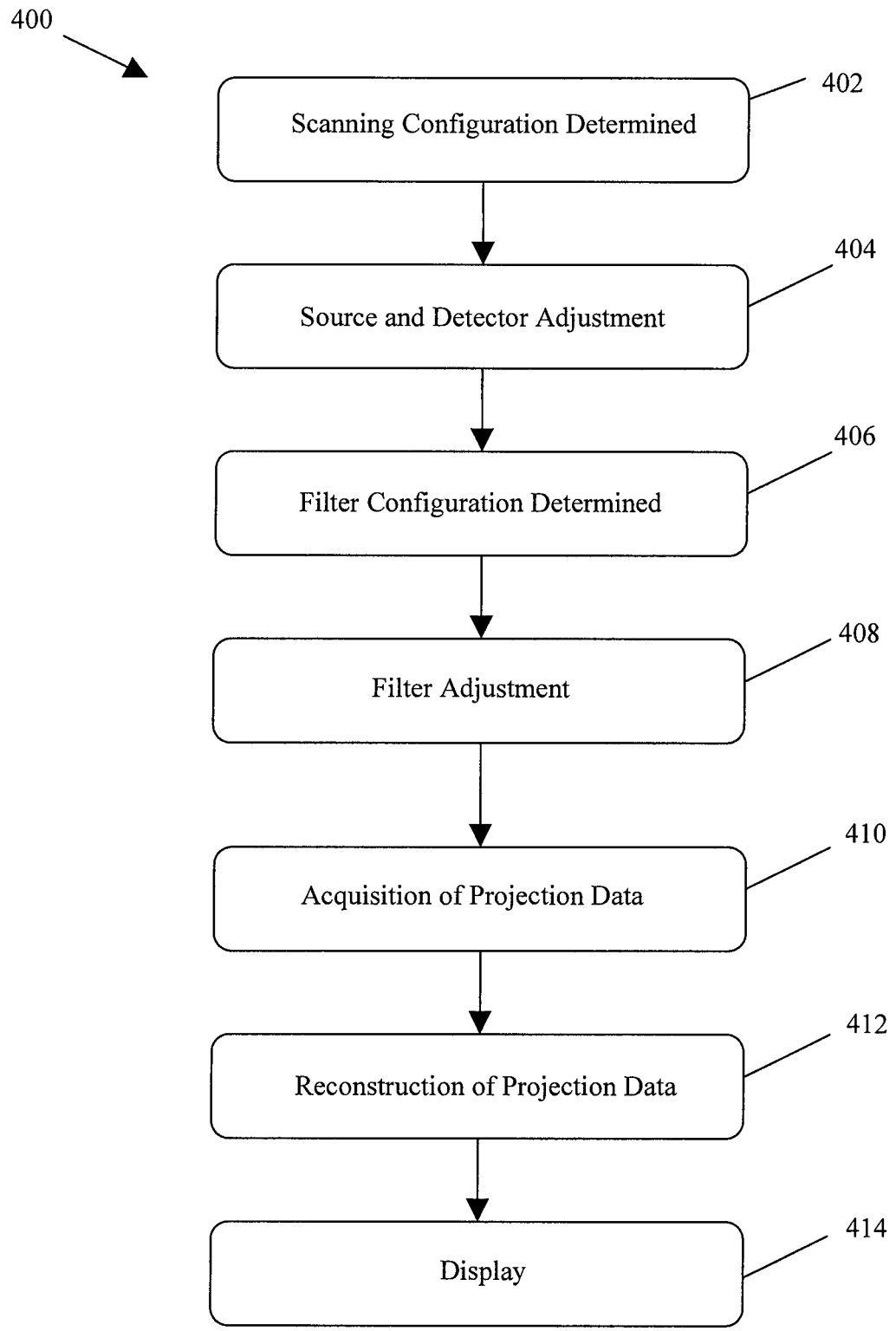

FIG. 3 schematically depicts an imaging system according to an embodiment of the invention; and FIG. 4 depicts an imaging method according to an embodiment of the invention.

Figure 1:
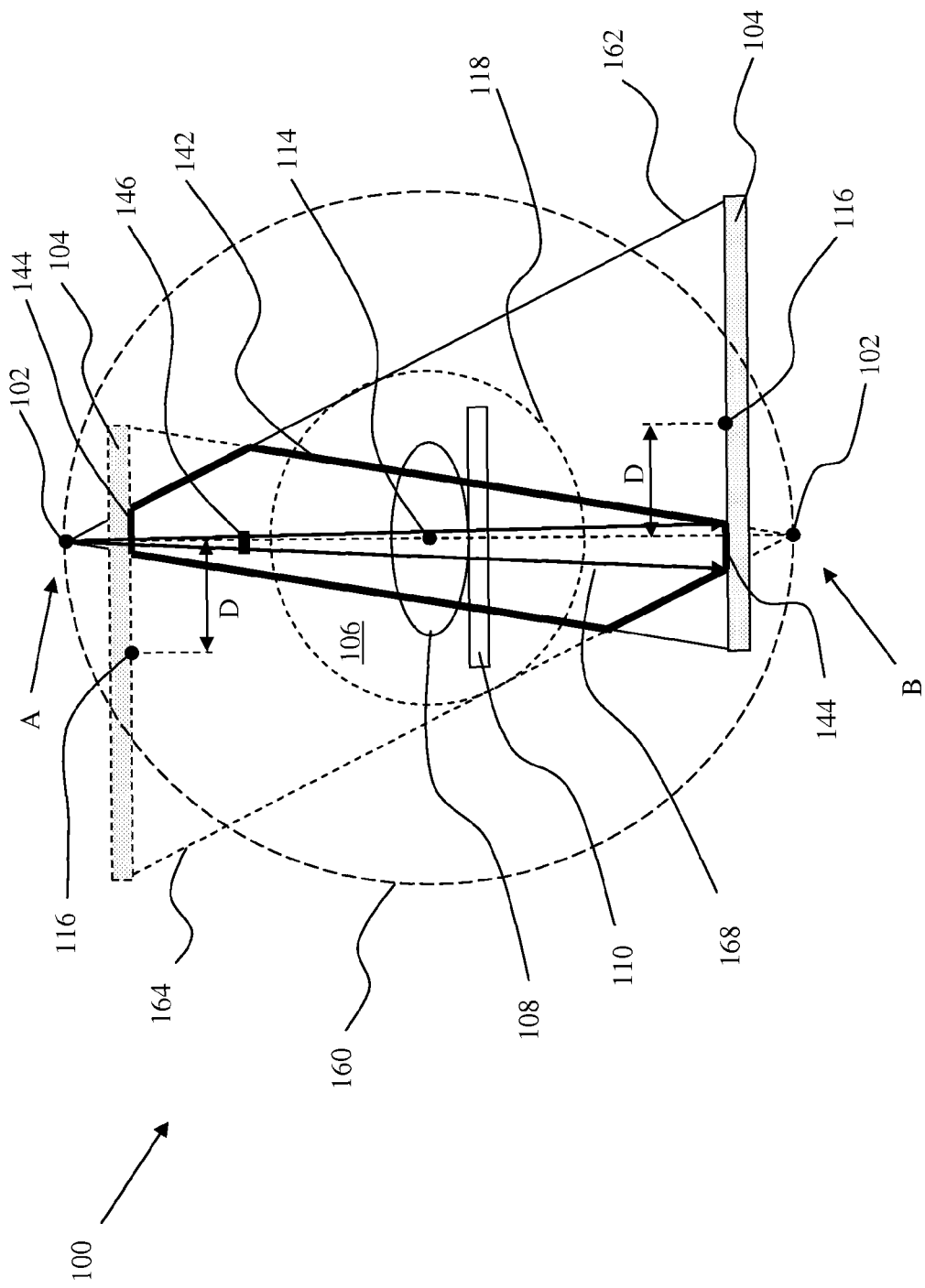
FIG. 1 is a transaxial view of a displaced CT acquisition geometry in the transaxial plane according to an embodiment of the invention.

The present application is directed generally to a method and apparatus for filtering x-ray beams generated using an x-ray based imaging system such as a CT apparatus with displaced acquisition geometry. FIG. 1 depicts an exemplary CT apparatus geometry 100 having an x-ray source 102, such as an x-ray tube, and an x-ray sensitive detector 104, such as a flat panel area detector array extending in the transverse and axial directions. As shown, a transverse center 116 of the x-ray detector 104 is displaced or offset from a transverse center of rotation 114 in the transaxial plane. The source 102, on the other hand, is not offset in FIG. 1. However, both the x-ray source 102 and the x-ray detector 104 may be displaced from the transverse center of rotation 114 in other embodiments of the invention. A filter 146 for filtering some x-ray beams from the x-ray source 102 is shown located between the source 102 and the object 108 under examination in an examination region 106. As illustrated in FIG. 1, the transverse center of rotation 114 may also serve as the center of the transverse field of view ("FOV") 118. However, those two axes are not necessarily so aligned in every application. As illustrated, an object support 110 supports the object 108 under examination in the examination region 106.

While the figures and discussion are focused on the use of flat panel detectors, arcuate or otherwise shaped detectors may also be used. Further, while the figures and discussion focus on an x-ray CT system in which the x-ray source 102 is the focal spot of an x-ray tube and hence substantially a point source, other alternatives are contemplated. For example, the x-ray source 102 may be implemented as a line source. Wedge and other beam geometries are also contemplated. In addition, while the principal application is an x-ray based system, gamma and other radiation sources may also be used. Multiple x-ray sources 102 and x-ray detectors 104 may also be provided, in which case corresponding sets of sources and detectors may be offset angularly and/or longitudinally from one another.

As illustrated in FIG. 1, the x-ray source 102 and the x-ray sensitive detector 104 rotate about the transverse center of rotation 114. The source 102 and detector 104 are generally mounted to a rotating gantry (not shown) for rotation about the examination region 106. An exemplary rotation trajectory 160 of the source 102 is illustrated by a dashed circle in FIG. 1. In some embodiments, however, the source 102 and detector 104 may remain at a constant angular position while the object 108 is moved and/or rotated to produce the requisite angular sampling.

As illustrated in FIG. 1, the x-ray source 102 and detector 104 of the CT apparatus geometry 100 are depicted in two different and opposing positions in the transaxial plane. In position A (solid lines), the source 102 is disposed above the object 108 and the detector 104 is disposed below the object. In position B, the x-ray source 102 and detector 104 are rotated about the transverse center of rotation 180 degrees from position A. Thus, in position B (dotted lines), the source 102 is below the object 108 and the detector 104 is above the object. In both positions A and B, the transverse center 116 of the detector 104 remains offset a distance D from the transverse center of rotation 114.

As illustrated in FIG. 1, the cone 162 of radiation generated by the source 102 in position A intersects with the cone 164 of radiation generated with the source 102 in position B. The region 142 in which the cones 162, 164 intersect is shown in FIG. 1 bounded by bold lines. The area 144 of the detector 104 that receives overlapping radiation (e.g., projection 168 in position A) is also shown in bold lines. This overlap area 144 remains in the same location relative to the transverse center 116 of the detector 104 as the detector rotates about the transverse center of rotation 114. The amount of overlap for a particular configuration of the source 102 and the detector 104 is the percentage of the total surface area of the detector that receives the overlapping radiation. The amount of overlap may be optimized based on various factors, such as the estimated size of the object 108 under examination, the scan protocol, etc.

The amount of overlap may be varied by varying the distance D between the transverse center 116 of the detector 104 and the transverse center of rotation 114. However, increasing the amount of overlap decreases the size of the transverse FOV 118. For example, decreasing the distance D increases the amount of overlap and decreases the size of the transverse FOV 118. Conversely, increasing the distance D decreases the amount of overlap and increases the size of the transverse FOV 118.

Maximum overlap of the radiation occurs at full beam geometry. Full beam geometry corresponds to the situation where the transverse center 116 of the detector 104 intersects the transverse center of rotation 114 (i.e., where D=0). There is zero overlap of the radiation when the distance D is equal to or greater than one half the detector 104 width. Zero overlap provides for a maximum size of the transverse FOV 118. Further, in a zero overlap configuration, a rotation of approximately 360 degrees is needed to obtain a complete angular sampling, whereas a rotation of 180 degrees plus the fan or cone angle provides a complete angular sampling when configured in the full beam geometry. The requisite angular range for intermediate configurations varies between 180 degrees plus the fan angle and 360 degrees, and can readily be calculated from the geometry of the system 100.

The amount of overlap can vary between minimum overlap (i.e., zero overlap) and maximum overlap (i.e., full beam geometry). However, as stated, overlap projection data is generally useful in connection with reconstruction algorithms (e.g., the filtering part of the backprojection) to generate volumetric data indicative of the object under examination 108. It is believed that a minimum of about 5% overlap (i.e., 5% of the total surface area of the detector 104) is useful in connection with the reconstruction algorithm. Further, the amount of overlap must be balanced against the size of the transverse FOV 118. For example, increasing the overlap amount above about 25% may result in the transverse FOV 118 being too small to scan the entire object. Thus, in a preferred embodiment, the amount of overlap is between about 5% and about 25% of the total surface area of the detector 104. For example, in one embodiment, the amount of overlap is between about 9% and 10%, or about 9.5%, of the total surface area of the detector 104. In another embodiment, the amount of overlap is about 7.5% of the total surface area of the detector 104.

As illustrated in FIG. 1, a filter 146 is placed in the path of the overlapping radiation (e.g., projection 168) generated with the source 102 and the detector 104 in position A. Although not shown in FIG. 1, the filter 146 remains in the path of the overlapping radiation as the source 102 and the detector 104 rotate about the transverse center of rotation 114, thus filtering the overlapping radiation regardless of the position of the source and the detector (e.g., when the source and detector are in position B). The filter 146 may be placed in the path of the overlapping radiation at any location between the source 102 and detector 104. However, disposing the filter 146 between the source 102 and the object 108 under examination (e.g., a patient) provides the benefit of reducing the x-ray dosage received by the object.

As illustrated in FIG. 1, the filter 146 is configured to reduce the amount of x-ray dosage received by the object 108 under examination by absorbing, or blocking, a percentage of the overlapping radiation. The percentage of overlapping radiation absorbed or blocked by the filter 146 (i.e., the filter's strength) may be controlled by varying at least one of the size and shape of the filter or the type of filter material. For example, a thick filter is generally able to absorb or block more x-rays than a thin filter of the same or similar material. Further, different filter materials are able to absorb or block different amounts and wavelengths of the overlapping radiation. In some embodiments, more than one filter may be used to absorb or block the overlapping radiation. Filters of different materials, sizes, and/or shapes may be interchanged, added, or removed automatically (e.g., with one or more drives) or manually by a human user. Such actions may be as specifically directed by a human user, or according to pre-set operating protocols.

The filter 146 may be made from any suitable material capable of absorbing or blocking a percentage of the radiation impinging upon the filter 146. For example, the filter 146 may be at least one or any combination of copper, aluminum, beryllium, tungsten, and lead. Any one or more of these materials may alter the spectral distribution of the x-rays. However, this alteration of the spectral distribution may generally be accounted for in processing the data produced by the detector 104. The exemplary filter 146 is a copper plate that absorbs about 50% of the x-rays in projection 168 impinging upon the filter 146. With such a filter, and assuming the amount of overlap is about 10%, the filter 146 absorbs about 5% of the total x-ray dosage generated by the x-ray source 102.

The size and location of the filter 146 may also vary based on the configuration of the source 102 and the detector 104. As stated, the amount of overlap may be varied by varying the distance D between the transverse center 116 of the detector 104 and the transverse center of rotation 114. As such, the size of the filter 146 (e.g., the width of the filter in the transaxial plane) may vary such that it absorbs or blocks the overlapping radiation produced by the source 102 with the detector 104 in various configurations with various amounts of overlap. Further, the location of the filter 146 in the path of the overlapping radiation may vary (e.g., toward or away from the object 108 under examination in the transaxial plane) such that the filter absorbs or blocks the overlapping radiation produced by the source 102 with the detector 104 in various configurations with various amounts of overlap. The size and location of the filter 146 may be varied automatically (e.g., with one or more drives) or manually by a human user.

The filter 146 also provides for a more homogenous SNR distribution in the reconstructed image of the object 108 under examination. For each pair of opposing positions, some voxels in the image are reconstructed using the projection data from both views (e.g., position A and position B) while other voxels are reconstructed using projection data from one view only. For the voxels reconstructed using projection data from both views (i.e., overlapping projection data voxels), the amount of x-ray dosage per voxel is greater than the amount of the x-ray dosage per voxel for the voxels reconstructed using projection data from one view only (i.e., non-overlapping projection data voxels). The overlapping projection data voxels also appear differently than the non-overlapping projection data voxels in the reconstructed image at least due to the increase in x-ray dosage. Therefore, the reconstructed image has an inhomogeneous SNR distribution. The filter 146 absorbs a percentage of the overlapping radiation such that the x-ray dosage per voxel for the overlapping projection data voxels is reduced to correspond more closely with the x-ray dosage per voxel for the non-overlapping projection data voxels. Thus, the filter 146 provides for a more homogenous SNR distribution in the reconstructed image of the object 108 under examination.

For example, a standard exposure from a simulated CT scan with no x-ray dose reduction in the area of the detector receiving the overlapping radiation is shown in FIG. 2A. As shown, the exposure yields an inhomogeneous illumination in which the bright circle in the transverse center represents the area of the detector which receives the overlapping radiation, or the overlap area 202. The area of the exposure surrounding the overlap area 202 represents the non-overlapping area 204 of the detector. An exposure from a simulated CT scan with a 50% x-ray dose reduction in the area of the detector receiving the overlapping radiation, or overlap area 212, is shown in FIG. 2B. As shown, the exposure yields a more homogeneous illumination in the image as a whole. That is, the overlap area 212 in FIG. 2B (with dose reduction) is darker than the overlap area 202 in FIG. 2A (without dose reduction). Thus the darker overlap area 212 is more homogenous with the surrounding non-overlapping area 214 of the detector. For these simulations, the amount of detector overlap was assumed to be about 9.5%.

In many embodiments, a filter that absorbs about 50% of the overlapping x-ray radiation is desirable to reduce the amount of x-ray dosage and provide for a homogeneous SNR distribution in the reconstructed image. However, the amount of overlapping radiation absorbed by the filter 146 may vary based on the x-ray attenuation properties of the object 108 under examination in the area of the overlapping radiation. For example, if the x-ray attenuation properties of the object 108 in the area of the overlapping radiation is low (e.g., certain types of tissues), a stronger filter may be used to provide for a more homogeneous SNR distribution in the reconstructed image. Conversely, if the x-ray attenuation properties of the object 108 in the area of the overlapping radiation is high (e.g., bone), a weaker filter may be used to provide for a more homogeneous SNR distribution in the reconstructed image. Thus, in some embodiments the filter amount is modified by the user or by a selected protocol.

The filter 146 may also be used in multimodality systems. For example, the filter 146 may be used in a combination single photon emission computed tomography ("SPECT") and CT system or a combination positron emission tomography ("PET") and CT system.

FIG. 3 schematically depicts an imaging system 302 suitable for use with the exemplary CT apparatus geometry 100. The system 302 includes a data acquisition system 304, a reconstructor 306, an image processor 308, a user interface 310, and a controller 312.

The data acquisition system 304 includes a CT data acquisition system 314 in which the source 102, detector 104, and filter 146 are mounted to a rotating gantry 316 for rotation about the examination region. Circular, 360 degrees or other angular sampling ranges as well as axial, helical, circle and line, saddle, or other desired scanning trajectories may be implemented, for example by moving the object support 110 longitudinally in coordination with rotation of the rotating gantry 316.

In one implementation, the source 102, detector 104, and filter 146 are fixedly mounted in relation to the rotating gantry 316 so that the acquisition geometry is fixed. In another, the source 102, detector 104, and filter 146 are movably mounted to the rotating gantry 316 so that the acquisition geometry is variable, for example to allow the relative movement described above. In such an implementation, one or more drives 318 may provide the requisite motive force. Alternately, the source 102, detector 104, and filter 146 may be moved manually by a human user.

A reconstructor 306 reconstructs the data generated by the data acquisition system 304 using reconstruction techniques to generate volumetric data indicative of the object under examination. Reconstruction techniques include analytical techniques such as filtered backprojection, as well as iterative techniques.

An image processor 308 processes the volumetric data as required, for example for display in a desired fashion on a user interface 310, which may include one or more output devices such as a monitor and printer and one or more input devices such as a keyboard and mouse.

The user interface 310, which is advantageously implemented using software instructions executed by a general purpose or other computer so as to provide a graphical user interface ("GUI"), allows the user to control or otherwise interact with the imaging system 302. For example, the user may select one or more of a desired FOV (i.e., overlap) and filter configuration or dimension; initiate and/or terminate scans; select desired scan or reconstruction protocols; manipulate the volumetric data; and the like. In one implementation, one or more of the FOV configuration, overlap configuration, filter configuration, and reconstruction protocol are established automatically by the imaging system 302 based on a scan protocol selected by the user. As yet another example, the user interface 310 may prompt or otherwise allow the user to enter one or more of a desired FOV dimension, amount of overlap, filter type, and filter dimension. In such an implementation, the information from the user is used to automatically calculate the requisite position(s) of the source 102, detector 104, and/or filter 146.

A controller 312 operatively connected to the user interface 310 controls the operation of the data acquisition system 304, for example to carry out a desired scan protocol, or to cause the drive(s) 318 to position the source 102, detector 104, and/or filter 146.

The imaging system may also be used with multimodality systems and geometries. For example, the imaging system may be used with a combination SPECT and CT system or a combination PET and CT system.

The aforementioned functions, such as for example, selecting one or more of a desired FOV, overlap, and filter configuration or dimension; initiating and/or terminating scans; selecting desired scan or reconstruction protocols; manipulating the volumetric data; and the like, can be performed as software logic. "Logic," as used herein, includes but is not limited to hardware, firmware, software and/or combinations of each to perform a function(s) or an action(s), and/or to cause a function or action from another component. For example, based on a desired application or needs, logic may include a software controlled microprocessor, discreet logic such as an application specific integrated circuit (ASIC), or other programmed logic device. Logic may also be fully embodied as software.

"Software," as used herein, includes but is not limited to one or more computer readable and/or executable instructions that cause a computer or other electronic device to perform functions, actions, and/or behave in a desired manner. The instructions may be embodied in various forms such as routines, algorithms, modules or programs including separate applications or code from dynamically linked libraries. Software may also be implemented in various forms such as a stand-alone program, a function call, a servlet, an applet, instructions stored in a memory, part of an operating system or other type of executable instructions. It will be appreciated by one of ordinary skill in the art that the form of software is dependent on, for example, requirements of a desired application, the environment it runs on, and/or the desires of a designer/programmer or the like.

The systems and methods described herein can be implemented on a variety of platforms including, for example, networked control systems and stand-alone control systems. Additionally, the logic, databases or tables shown and described herein preferably reside in or on a computer readable medium, such as a component of the imaging system 302. Examples of different computer readable media include Flash Memory, Read-Only Memory (ROM), Random-Access Memory (RAM), programmable read-only memory (PROM), electrically programmable read-only memory (EPROM), electrically erasable programmable read-only memory (EEPROM), magnetic disk or tape, optically readable mediums including CD-ROM and DVD-ROM, and others. Still further, the processes and logic described herein can be merged into one large process flow or divided into many sub-process flows. The order in which the process flows herein have been described is not critical and can be rearranged while still accomplishing the same results. Indeed, the process flows described herein may be rearranged, consolidated, and/or re-organized in their implementation as warranted or desired.

For example, such a process 400 is shown in FIG. 4. Initially, as shown in FIG. 4, a scanning configuration is determined at step 402. The scanning configuration may include determining the offset of the x-ray detector 104 and/or source 102 for a desired FOV configuration and therefore amount of overlap. The desired FOV configuration and amount of overlap may be determined using any of the methods described above or other methods. At least a minimal amount of overlap projection data is generally useful in connection with reconstruction algorithms (e.g., the filtering part of the backprojection) to generate volumetric data indicative of the object under examination. Because the size of the FOV decreases as the amount of overlap increases, the amount of overlap can be balanced against the desired size of the FOV. The amount of offset may vary between the scans taken at various angular positions about the examination region 106 and along the longitudinal axis. The positions of the detector 104 and/or source 102 are adjusted at step 404 to provide the desired FOV configuration and amount of overlap.

A filter configuration is determined at step 406. The filter configuration includes determining the size and/or location of the filter 146 based on the configuration of the detector 104 and the source 102 and the amount of overlap. The size and location of the filter 146 may be determined using any of the methods described above or other methods. For example, the filter 146 size (e.g., the width of the filter in the transaxial plane) may be determined based on the amount of overlap such that the filter absorbs or blocks at least a portion of the overlapping x-ray radiation. Further, the filter 146 location in the path of the overlapping x-ray radiation (e.g., toward or away from the object 108 under examination in the transaxial plane) may be determined based on the amount of overlap such that the filter absorbs or blocks the overlapping x-ray radiation. The size and/or location of the filter 146 may vary between the scans taken at various angular positions about the examination region 106 and along the longitudinal axis.

The filter configuration may also include determining a desirable amount of reduction in the overlapping x-ray radiation to reduce the amount of x-ray dosage and provide for a homogeneous SNR distribution in the reconstructed image. The amount of reduction in the overlapping x-ray radiation may be determined using any of the methods described above or other methods. For example, the amount of reduction in the overlapping x-ray radiation may be determined based on the x-ray attenuation properties of the object 108 under examination in the area of the overlapping radiation. The percentage of overlapping radiation absorbed or blocked by the filter 146 (i.e., the filter's strength) may vary based on at least the size (e.g., thickness) and shape of the filter, type of filter material, and number of filters. The amount of reduction in the overlapping x-ray radiation may vary between the scans taken at various angular positions about the examination region 106 and along the longitudinal axis.

One or more of the size and location of the filter 146 are adjusted at step 408 to absorb or block the overlapping x-ray radiation for the desired FOV configuration and amount of overlap. Further, one or more of the size, shape, and material of the filter(s) may be adjusted at step 408 to absorb or block a desired amount of the overlapping x-ray radiation. In some embodiments, the positions of the detector 104 and/or source 102 are also adjusted at step 408 (instead of step 404) to provide the desired FOV configuration and amount of overlap.

A scan is taken at step 410 so as to acquire projection data at various angular positions as the gantry 316 rotates about the examination region 106. The projection data is reconstructed at step 412 and displayed on the user interface 310 at step 414. The process 400 may be repeated as desired, for example to scan a succession of patients. Note that additional scan(s) may be obtained prior to reconstructing and/or displaying the data acquired in given scan.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. An apparatus for acquiring tomographic projection data at a plurality of angular positions relative to an object disposed in an examination region, the apparatus comprising:
    a radiation source, wherein at least a portion of radiation emitted by the source at a first angular position (A) overlaps with at least a portion of radiation emitted by the source at a second angular position (B) opposite the first angular position;
    a radiation sensitive detector which detects radiation that has traversed the examination region, wherein a transverse center of the detector is transversely displaced from a transverse center of a transverse field of view during acquisition of the projection data; and
    a filter which absorbs at least a portion of the overlapping radiation such that at least a portion of the overlapping radiation is absorbed more than non-overlapping radiation.

2. The apparatus of claim 1, wherein the detector can move to vary an amount of transverse displacement (D).

3. The apparatus of claim 1, wherein an area of the detector corresponding to the overlapping radiation is between about 5% and about 25% of a total surface area of the detector.

4. The apparatus of claim 3, wherein the area of the detector corresponding to the overlapping radiation is between about 6% and about 10% of the total surface area of the detector.

5. The apparatus of claim 1, wherein the filter is disposed between the source and the object.

6. The apparatus of claim 5, wherein at least an amount of overlapping radiation determines the location of the filter relative to the source and the object.

7. The apparatus of claim 1, wherein at least an amount of overlapping radiation determines the size of the filter.

8. The apparatus of claim 1, wherein the filter reduces an amount of radiation dosage per voxel in a reconstructed image of the object such that the signal to noise ratio among the voxels in the reconstructed image is substantially homogeneous.

9. The apparatus of claim 1, wherein at least an attenuation property of the object determines at least one of a size of the filter, a shape of the filter, and a type of filter material.

10. The apparatus of claim 1, wherein more than one filter absorbs at least a portion of the overlapping radiation.

11. The apparatus of claim 1, wherein at least one of a location of the filter, a size of the filter, a shape of the filter, and a type of filter material is adjusted by a drive.

12. The apparatus of claim 1, wherein the filter comprises at least one of copper, aluminum, beryllium, tungsten, and lead.

13. A computed tomography method, comprising the steps of:
acquiring tomographic projection data at a plurality of angular positions relative to an object disposed in an examination region, using a radiation source, a radiation sensitive detector which detects radiation emitted by the source that has traversed the examination region, and a filter, wherein at least a portion of the radiation emitted by the source at a first angular position (A) overlaps with at least a portion of the radiation emitted by the source at a second angular position (B) opposite the first angular position, a transverse center of the detector is transversely displaced from a transverse center of a transverse field of view during acquisition of the projection data, and the filter absorbs at least a portion of the overlapping radiation such that at least a portion of the overlapping radiation is absorbed more than non-overlapping radiation.

14. The method of claim 13 further comprising determining an amount of transverse displacement (D) of at least the transverse center of the detector from the transverse center of the transverse field of view and adjusting the transverse center of the detector to correspond to the amount of determined transverse displacement.

15. The method of claim 13 further comprising determining at least one of the transverse width and location of the filter based on the amount of overlapping radiation and adjusting the filter to correspond to the at least one of the determined transverse width and location of the filter in the path of the overlapping radiation.

16. The method of claim 13 further comprising using the acquired tomographic projection data to generate a CT image of the imaged object.

17. The method of claim 13 further comprising determining at least one of a size of the filter, a shape of the filter, and a type of filter material for absorbing a desired amount of overlapping radiation and adjusting the filter to correspond to at least one of the determined size of the filter, shape of the filter, and type of filter material.

18. The method of claim 13 further comprising determining an attenuation property of the object and adjusting the filter to correspond to the determined attenuation property of the object.

19. The method of claim 13 further comprising determining a number of filters for absorbing a desired amount of overlapping radiation and adjusting the filter to correspond to the determined number of filters.

20. The method of claim 13 further comprising determining an amount of overlapping radiation to be absorbed by the filter for a desired reduction in radiation dosage received by the object and adjusting the filter to correspond to the determined amount of overlapping radiation.

21. The method of claim 13 further comprising determining an amount of overlapping radiation to be absorbed by the filter for a desired reduction in the amount of radiation dosage per voxel in a reconstructed image of the object such that the signal to noise ratio among the voxels in the reconstructed image is substantially homogeneous, and adjusting the filter to correspond to the determined amount of overlapping radiation.

22. The method of claim 13, wherein the amount of overlapping radiation absorbed by the filter is modified by at least one of a user or a selected protocol.

23. A CT imaging system for acquiring tomographic projection data at a plurality of angular positions relative to an object disposed in an examination region, the system comprising:
a data acquisition system having,
a radiation source, wherein at least a portion of radiation emitted by the source at a first angular position (A) overlaps with at least a portion of radiation emitted by the source at a second angular position (B) opposite the first angular position,
a radiation sensitive detector which detects radiation that has traversed the examination region, wherein a transverse center of the detector is transversely displaced from a transverse center of a transverse field of view during acquisition of the projection data, and
a filter which absorbs at least a portion of the overlapping radiation such that at least a portion of the overlapping radiation is absorbed more than non-overlapping radiation;
a reconstructor to reconstruct the projection data generated by the data acquisition system to generate volumetric data indicative of the object;
an image processor that processes the volumetric data for display on a user interface; and
a controller to control the operation of the data acquisition system.

24. The imaging system of claim 23 further comprising a single photon emission computed tomography system.

25. The imaging system of claim 23 further comprising a positron emission tomography system.

* * * * *